United States Patent
Maier et al.

(10) Patent No.: US 11,718,653 B2
(45) Date of Patent: Aug. 8, 2023

(54) METHOD FOR IN VITRO GLYCOENGINEERING OF AN ERYTHROPOIESIS STIMULATING PROTEIN

(71) Applicant: Hoffmann-La Roche Inc., Little Falls, NJ (US)

(72) Inventors: Maria Maier, Penzberg (DE); Marco Thomann, Beuerberg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 150 days.

(21) Appl. No.: 17/124,254

(22) Filed: Dec. 16, 2020

(65) Prior Publication Data

US 2021/0101950 A1 Apr. 8, 2021

Related U.S. Application Data

(63) Continuation of application No. 16/574,467, filed on Sep. 18, 2019, now abandoned, which is a continuation of application No. PCT/EP2018/056725, filed on Mar. 16, 2018.

(30) Foreign Application Priority Data

Mar. 20, 2017 (EP) .................... 17161883

(51) Int. Cl.
*C07K 14/47* (2006.01)
*C12P 21/02* (2006.01)
*C07K 14/505* (2006.01)

(52) U.S. Cl.
CPC ............ *C07K 14/505* (2013.01); *C12P 21/02* (2013.01)

(58) Field of Classification Search
CPC ........... C12N 9/10; C07K 16/00; C12P 21/00; C12Q 1/00
See application file for complete search history.

(56) References Cited

FOREIGN PATENT DOCUMENTS

| EP | 0148605 B2 | 12/1998 |
| EP | 0205564 B2 | 6/2000 |
| EP | 2664192 B1 | 6/2016 |
| EP | 2042196 B1 | 7/2016 |
| EP | 3570871 B1 | 11/2020 |
| WO | 2004/099231 A2 | 11/2004 |
| WO | 2008/057683 A2 | 5/2008 |
| WO | 2012/094627 A2 | 12/2012 |

OTHER PUBLICATIONS

Boeggeman et al., "Studies on the metal binding sites in teh catalytic domain of β1,4-galactosyltransferase" Glycobiology 12(7):395-407 (2002).
Egrie et al., "Characterization and biological effects of recombinant human erythropoietin" Immunobiol 172:213-224 ( 1986).
Extended European Search Report for EP Application No. 17161883. 8.. pp. 11 (dated Jul. 17, 2017).
Fukuda et al., "Survival of Recombinant Erythropoietin in the Circulation: The ROle of Carbohydrates" Blood 73(1):84-89 (1989).
Hummel et al., "Elongation of N-acetyllactosamine repeats in diantennary oligosaccharides" Eur J Biochem 245:428-433 ( 1997).
Inoue et al., "The production of recombinant human erythropoietin" Biotech Ann Rev. 1:297-313 ( 1995).
International Preliminary Report on Patentability for PCT/EP2018/056725 completed on Mar. 21, 2019.
International Search Report for PCT/EP2018/056725 dated May 18, 2018.
Shahrokh et al., "Erythropoietin Produced in a Human Cell Line (Dynpo) Has Significant Differences in Glycosylation Compared with Erythropoietins Produced in CHO Cell Lines" Molecular Pharmaceutics 8(1):286-296 ( 2011).

Primary Examiner — Maryam Monshipouri
(74) Attorney, Agent, or Firm — Cindy S. Shu (57) ABSTRACT

The present invention relates to a method for the production of in vitro glycoengineered erythropoiesis stimulating protein, comprising the steps of providing sialic acid free erythropoiesis stimulating protein, treating the erythropoiesis stimulating protein with N-Acetyl-Glucosamin-transferase B3GNT2, treating the erythropoiesis stimulating protein with galactosyltransferase, and treating the erythropoiesis stimulating protein with sialyltransferase.

9 Claims, 2 Drawing Sheets
Specification includes a Sequence Listing.

METHOD FOR IN VITRO GLYCOENGINEERING OF AN ERYTHROPOIESIS STIMULATING PROTEIN

CROSS REFERENCE TO RELATED APPLICATIONS

This application is a continuation of U.S. patent application Ser. No. 16/574,467, filed Sep. 18, 2019, which is a continuation of International Application No. PCT/EP2018/056725, filed Mar. 16, 2018, which claims priority to European Patent Application No. 17161883.8, filed Mar. 20, 2017, each of which are incorporated herein by reference in its entirety.

SEQUENCE LISTING

This application contains a Sequence Listing which has been submitted electronically in ASCII format and is hereby incorporated by reference in its entirety. Said ASCII copy, created on Dec. 7, 2020, is named P34172-US-1-SeqList.txt and is 17,819 bytes in size.

FIELD OF THE INVENTION

The present invention relates to an in vitro glycoengineered erythropoiesis stimulating protein, methods for the production of said erythropoiesis stimulating protein and uses thereof.

BACKGROUND OF THE INVENTION

Erythropoiesis stimulating proteins are glycoproteins comprising several N-glycosylation sites. Variation of the glycan pattern on proteins has enormous implications on protein function. For example, the structure of the N-linked glycans on a protein can impact various characteristics, including the protease susceptibility, intracellular trafficking, secretion, tissue targeting, biological half-life and antigenicity of the protein in a cell or organism. The alteration of one or more of these characteristics greatly affects the efficacy of a protein in its natural setting, and also affects the efficacy of the protein as a therapeutic agent in situations where the peptide has been generated for that purpose.

Figure 1:
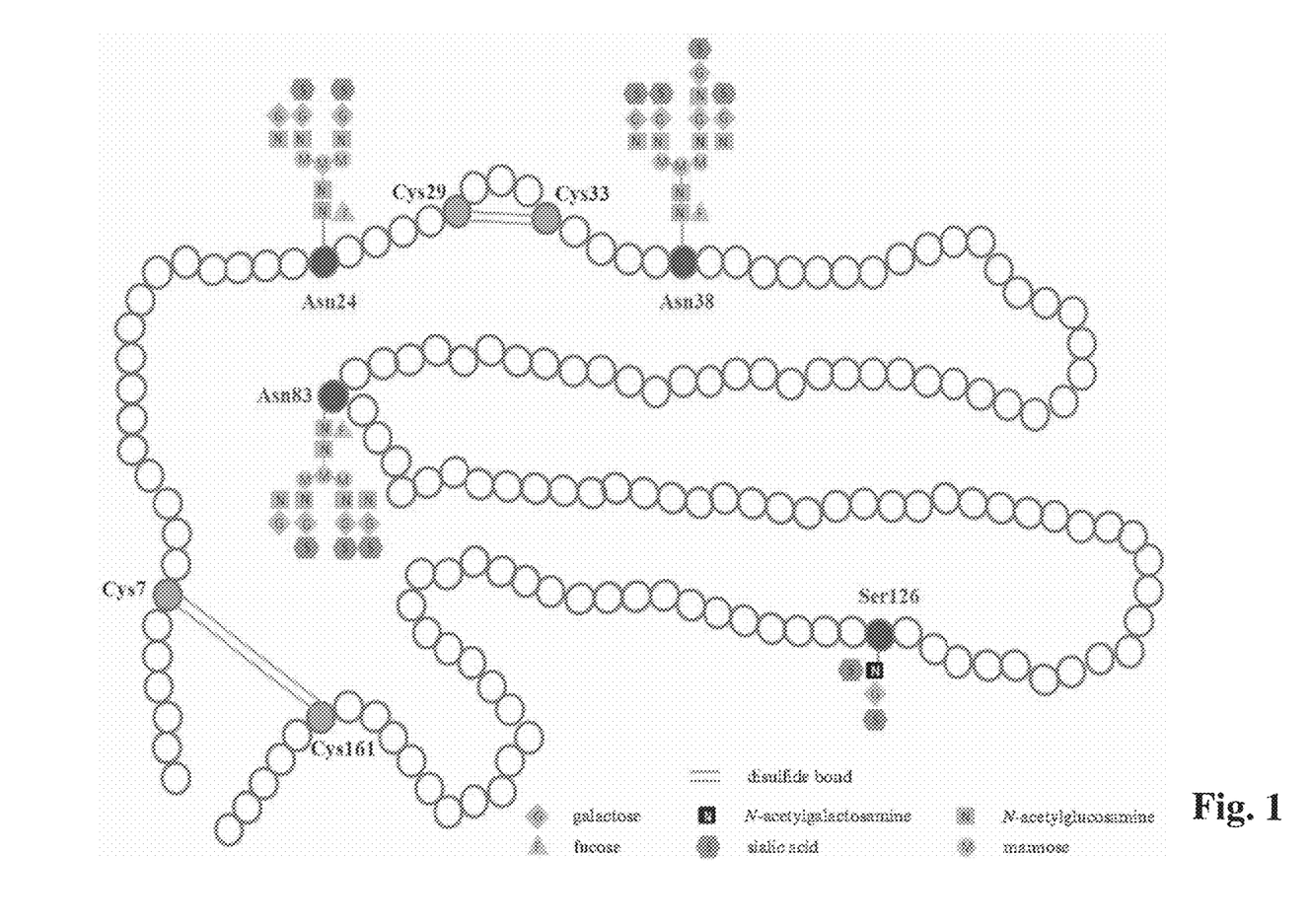
FIG. 1: Structure of EPO and its glycosylation sites (adapted from Postnikov et al 2016 Russ. Chem. Rev. 85 99)

Erythropoietin (EPO) is a glycoprotein with three N-glycosylation sites and one O-glycosylation site. Erythropoietin has been manufactured biosynthetically using recombinant DNA technology (Egrie, J C, Strickland, T W, Lane, J et al. (1986) Immunobiol. 72: 213-224) and is the product of a cloned human EPO gene inserted into and expressed in the ovarian tissue cells of the Chinese hamster (CHO cells). The primary structure of the predominant, fully processed form of human erythropoietin (hEPO) is illustrated in FIG. 1. There are two disulfide bridges; between Cys7-Cys161 and Cys29-Cys33. The molecular weight of the polypeptide chain of EPO without the sugar moieties is 18,236 Da. In the intact EPO glycoprotein, approximately 40% of the molecular weight is accounted for by the carbohydrate groups that glycosylate the protein at glycosylation sites on the protein (Sasaki, H, Bothner, B, Dell, A and Fukuda, M (1987) J. Biol. Chem. 262: 12059).

Typical N-glycans of EPO include bi-, tri- and tetraantennary structures with one or two N-acetyl lactosamine repeats (see e.g. Postnikov et al. 2016 Russ. Chem. Rev. 85 99).

It is known that a higher number of terminal sialic acid moieties on N-glycans of EPO is associated with a higher specific activity of EPO when compared to less sialylated EPO glycoproteins (see e.g. Imai et al., Eur. J. Biochem. 194 (1990), p. 457-462). Desialylation of EPO reduces the half-life of EPO in the circulation (Ridley et al. J Natl Med Assoc. 1994 February; 86(2):129-35).

A higher number of poly-N-acetyl lactosamine repeats or a higher number of branches of the N-glycans of EPO are both reported to be associated with a higher specific bioactivity of EPO, respectively (see e.g. WO 99/28346).

Is is known to modify the glycan pattern of EPO using genetically engineered host cells for the production of EPO, e.g. from WO 99/28346.

Methods for modifying the glycan pattern of glycoproteins in vitro, i.e. after production, are suggested. EP 2661492 discloses a method for improving the amount of alpha-2,6-sialylated glycans. EP 2664192 discloses that the circulation time of glycoproteins may be increased by increasing the number of poly-N-acetyl lactosamines, which is suggested to be achieved using a member of the beta3-N-acetyl-glucosamin transferase family (B3GNT1, 2, 3, 4).

WO 2008/57683 discloses a method for purification of EPO. It is suggested to remodel the glycan pattern of EPO in vitro using N-acetyl-glucosamin transferase and galactosyltransferase to form a glycosylated EPO polypeptide having at least one glycan residue with a terminal-GlcNAc-Gal moiety, preferably on mono-antennary branches.

EP 2042196 discloses a method for conjugating glycoproteins, e.g. EPO, with a modifying group (e.g. PEG) via glycan linkage. In order to provide for the optimal glycan pattern for adding the modifying group, the glycan pattern on the glycoprotein may be remodeled using different steps of glycosidation and (re-)glycosylation. In the disclosed method the sugar-coupled modifying group is linked to the glycoprotein using the respective sugar-specific glycosyltransferase. For coupling a sialic-acid-coupled modifying group it is suggested to modify the glycan pattern of EPO, e.g., by (a) sialidation and subsequent sialylation with the sialic-acid-coupled modifying group; (b) treatment with N-acetyl-glucosamin transferase, galactosyltransferase and sialyltransferase ST3; or (c) treatment with sialidase, galactosyltransferase and sialyltransferase ST3.

As the variation of the glycan pattern affects protein function, there is a need for a generally applicable method of producing erythropoiesis stimulating proteins having a desired and reproducible, i.e., a customized glycan pattern, e.g. for assuring a constant quality and/or improving the biological function and/or stability of the erythropoiesis stimulating protein.

SUMMARY OF THE INVENTION

The present invention relates to a method for the production of in vitro glycoengineered erythropoiesis stimulating protein, comprising the steps of
  a) providing sialic acid free erythropoiesis stimulating protein,
  b) treating the erythropoiesis stimulating protein with N-Acetyl-Glucosamin-transferase B3GNT2,
  c) treating the erythropoiesis stimulating protein with galactosyltransferase,
  d) treating the erythropoiesis stimulating protein with sialyltransferase.

One aspect of the invention relates to the use of the method according to the invention for increasing the number of poly-N-acetyl lactosamine repeats on N-glycans of the erythropoiesis stimulating protein.

Another aspect of the invention is the use of the method according to the invention for providing an erythropoiesis stimulating protein with a controlled number of poly-N-acetyl lactosamine repeats on their N-glycans.

Another aspect of the invention is the use of the method according to the invention for improving the specific activity of the erythropoiesis stimulating protein.

Another aspect of the invention is an in vitro glycoengineered erythropoiesis stimulating protein produced by a method of the invention.

In one embodiment of all aspects of the invention the erythropoiesis stimulating protein is erythropoietin.

The invention provides a method for generating in vitro glycoengineered erythropoiesis stimulating proteins with a controlled number of poly-N-acetyl lactosamine repeats. According to the invention an erythropoiesis stimulating protein can be in vitro glycoengineered resulting in a customized glycan pattern, which may assure a constant product quality and/or improve the biological function, like the specific bioactivity, of the erythropoiesis stimulating protein. With the invention the number of poly-N-acetyl lactosamine repeats on N-glycans of the erythropoiesis stimulating protein can be increased.

DESCRIPTION OF THE FIGURES

FIG. 2A-E: Typical glycosylation patterns of EPO.

DETAILED DESCRIPTION OF THE INVENTION

1. Definitions

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. The methods and techniques of the present disclosure are generally performed according to conventional methods well known in the art. Generally, nomenclatures used in connection with, and techniques of, biochemistry, enzymology, molecular, and cellular biology, microbiology, genetics and protein and nucleic acid chemistry and hybridization described herein are those well-known and commonly used in the art.

Unless otherwise defined herein the term "comprising of" shall include the term "consisting of".

The term "about" as used herein in connection with a specific value (e.g. temperature, concentration, time and others) shall refer to a variation of +/−1% of the specific value that the term "about" refers to.

As used herein, "erythropoiesis stimulating protein" means a protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. The variants, analogs, or derivatives of erythropoietin as meant herein comprise at least three N-glycosylation sites, in one embodiment the N-glycosylation sites are Asn24, Asn38 and Asn83. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Patent Application Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; 7,217,689; PCT publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; WO 2006/29094; and U.S. publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; 2006/0111279.

As used herein, the term "analogs", when used with reference to polypeptides, refers to an amino acid sequence that has insertions, deletions or substitutions relative to the parent sequence, while still substantially maintaining the biological activity of the parent sequence, as determined using biological assays known to one of skill in the art. As used herein, the term "derivatives" of naturally occurring or analog polypeptides means polypeptides have been chemically modified, for example, to attach water soluble polymers (e.g., pegylated), labels (e.g., radionuclides or various enzymes), or other diagnostic or targeting or therapeutic moieties, or by insertion or substitution of non-natural amino acids by chemical means. Such derivatives will retain the binding properties of underivatized molecules of the invention.

In one embodiment the "erythropoiesis stimulating protein" comprises 3 or more N-glycosylation sites.

In one embodiment the erythropoiesis stimulating protein is erythropoietin.

The term "erythropoietin" or "EPO" refers to a glycoprotein, having the amino acid sequence set out in SEQ ID NO:1. In one embodiment, this term includes an amino acid sequence substantially homologous to the sequence of SEQ ID NO:1, whose biological properties relate to the stimulation of red blood cell production and the stimulation of the division and differentiation of committed erythroid progenitors in the bone marrow. As used herein, these terms include such proteins modified deliberately, as for example, by site directed mutagenesis or accidentally through mutations. In an embodiment, the terms erythropoietin or EPO analog include analogs having from 1 to 6 additional sites for glycosylation, analogs having at least one additional amino acid at the carboxy terminal end of the glycoprotein, wherein the additional amino acid includes at least one glycosylation site, and analogs having an amino acid sequence which includes a rearrangement of at least one site for glycosylation. As used herein, "rearrangement" of a glycosylation site means the deletion of one or more glycosylation sites in naturally occurring EPO and the addition of one or more non-naturally occurring glycosylation sites. These terms include both natural and recombinantly produced human erythropoietin.

As used herein, the term "N-glycan" refers to an N-linked oligosaccharide, e.g., one that is attached by an asparagine N-acetylglucosamine linkage to an asparagine residue of a polypeptide. N-glycans have a common pentasaccharide core of Man3GlcNAc2 ("Man" refers to mannose; "Glc" refers to glucose; and "NAc" refers to N-acetyl; "GlcNAc" refers to N-acelylglucosamine). The pentasaccharide core may be fucosylated. The term "trimannose core" used with respect to the N-glycan also refers to the structure Man3GlcNAc2 ("Man3"). N-glycans differ with respect to the number of branches (antennae) comprising peripheral sugars (e.g., fucose [herein abbreviated as "Fuc"] and sialic acid) that are added to the Man3 core structure. N-glycans are classified according to their branched constituents (e.g., high mannose, complex or hybrid).

Abbreviations used herein, including abbreviations of sugars, are of common usage in the art. Other common abbreviations include "PNGase", which refers to peptide N-glycosidase F (EC 3.2.2.18). The substrate UDP-GlcNAc is the abbreviation for UDP-N-acetylglucosamine. The intermediate ManNAc is the abbreviation for N-acetylmannosamine. The intermediate ManNAc-6-P is the abbreviation for N-acetylmannosamine-6-phosphate. The intermediate Sia-9-P is the abbreviation for sialate-9-phosphate. The intermediate Cytidine monophosphate-sialic acid is abbreviated as "CMP-Sia." Sialic acid is abbreviated as "Sia," "Neu5Ac," "NeuAc" or "NANA" herein.

Figure 2:
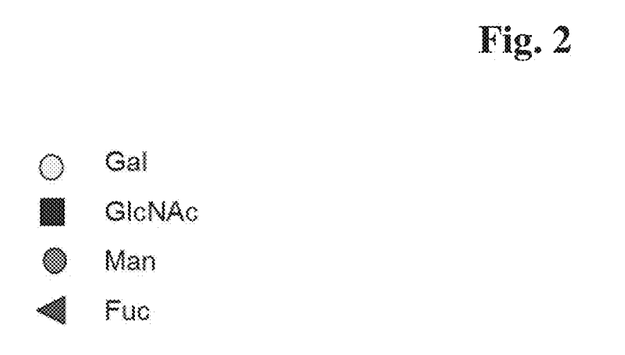
FIG. 2A: N-glycan with two branches.
FIG. 2B: N-glycan with three branches.
FIG. 2C: N-glycan with four branches.
FIG. 2D: N-glycan with four branches and one poly N-acetyl lactosamine repeat.
FIG. 2E: N-glycan with four branches and three poly N-acetyl lactosamine repeats.
Figure 2A:
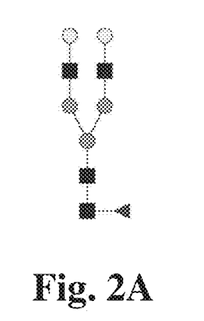
Figure 2B:
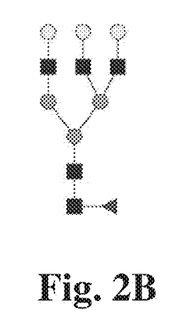
Figure 2C:
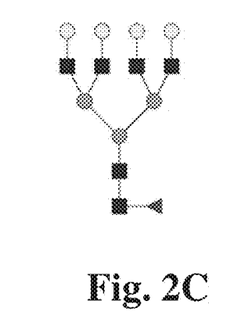

The N-glycans on erythropoiesis stimulating proteins, e.g. erythropoietin, include one or more N-acetyl lactosamine units bound to the pentasaccharide core structure of the N-linked oligosaccharide. The number of oligosaccharide "branches" as used herein refers to the number of individual oligosaccharide chains bound to the pentasaccharide core structure. E.g. as demonstrated in FIG. 2A two individual oligosaccharide chains are bound to the pentasaccharide core structure, hence, the N-glycan comprises two branches and is biantennary. E.g. as demonstrated in FIG. 2B three individual oligosaccharide chains are bound to the pentasaccharide core structure, hence, the N-glycan comprises three branches and is triantennary. E.g. as demonstrated in FIG. 2C four individual oligosaccharide chains are bound to the pentasaccharide core structure, hence, the N-glycan comprises four branches and is tetraantennary.

Figure 2D:
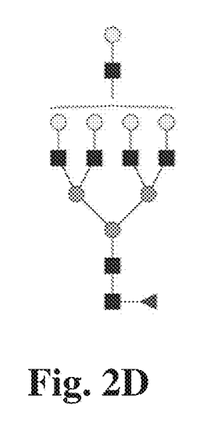
Figure 2E:
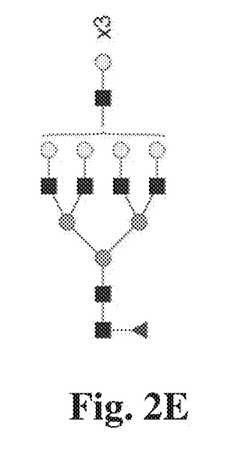

The N-glycans on erythropoiesis stimulating proteins, e.g. erythropoietin, include poly N-acetyl lactosamine units bound to the pentasaccharide core structure of the N-linked oligosaccharide. The term poly N-acetyl lactosamine "repeat" as used herein refers to the number of N-acetyl lactosamine units within one oligosaccharide branch minus one for the first N-acetyl lactosamine unit. E.g. as demonstrated in FIG. 2D two N-acetyl lactosamine units are present within one oligosaccharide branch, meaning that the oligosaccharide comprises one poly N-acetyl lactosamine repeat. E.g. as demonstrated in FIG. 2E four N-acetyl lactosamine units are present within one oligosaccharide branch, meaning that the oligosaccharide comprises three poly N-acetyl lactosamine repeats.

As used herein, the term "sialic acid" refers to a group of molecules where the common molecule includes N-acetyl-5-neuraminic acid (Neu5Ac) having the basic 9-carbon neuraminic acid core modified at the 5-carbon position with an attached acetyl group. Common derivatives of Neu5Ac at the 5-carbon position include: 2-keto-3-deoxy-d-glycero-d-galactononic acid (KDN) which possesses a hydroxyl group in place of the acetyl group; de-N-acetylation of the 5-N-acetyl group produces neuraminic (Neu); hydroxylation of the S—N-acetyl group produces N-glycolylneuraminic acid (Neu5Gc). The hydroxyl groups at positions 4-, 7-, 8- and 9- of these four molecules (Neu5Ac, KDN, Neu and Neu5Gc) can be further substituted with O-acetyl, O-methyl, O-sulfate and phosphate groups to enlarge this group of compounds. Furthermore, unsaturated and dehydro forms of sialic acids are known to exist.

The term "sialic acid free" as used herein refers to a population of erythropoiesis stimulating proteins that is substantially free from N-glycans comprising terminal sialic adic moieties. In one embodiment the term "sialic acid free" as used herein refers to a population of erythropoiesis stimulating proteins comprising a relative frequency of N-linked glycans that include a sialic acid moiety of 5% and less. In one embodiment, the sialic acid free erythropoiesis stimulating protein comprises a relative frequency of N-linked glycans that include a sialic acid moiety of about 0%.

The "relative frequency of N-linked glycans" as referred to herein means the percentage of a distinct glycan pattern within the population of erythropoiesis stimulating proteins related to all glycostructures within the population of erythropoiesis stimulating proteins. In one embodiment, the relative frequency of a population of erythropoiesis stimulating proteins refers to the percentage of a distinct glycan pattern within the population of erythropoiesis stimulating proteins related to all glycostructures identified by mass analysis of the entire protein (in one embodiment as described in example 2). In one embodiment, the relative frequency of a population of erythropoiesis stimulating proteins refers to the percentage of a distinct glycan pattern within the population of erythropoiesis stimulating proteins related to all glycostructures identified by mass analysis after enzymatic digest with endoproteinase Glu-C (LCMS peptide mapping, in one embodiment as described in example 1).

The term "in vitro glycoengineering" as referred to herein means the enzymatic alteration of the N-linked glycan structure of a erythropoiesis stimulating protein that is performed in vitro after the erythropoiesis stimulating protein is expressed in a recombinant expression system and, in one preferred embodiment, purified. In vitro glycoengineering within the terms of the invention may encompass the cleavage of at least one sugar residue from the N-linked glycan structure of at least a fraction of the erythropoiesis stimulating proteins comprised within the population of erythropoiesis stimulating proteins that was subject of in vitro glycoengineering. In vitro glycoengineering within the terms of the invention always encompasses also the addition of at least one sugar residue to the N-linked glycan structure of at least a fraction of the glycoproteins comprised within the population of erythropoiesis stimulating proteins that was subject of in vitro glycoengineering.

In vitro glycoengineering within the terms of the invention includes a series of steps of enzymatic treatments of erythropoiesis stimulating proteins that were expressed in a recombinant expressions system and, in one preferred embodiment, purified. In one embodiment said enzymatic treatment includes at least one step of enzymatic treatment with an enzyme capable of cleaving a terminal sugar residue from an N-linked oligosaccharide structure of the erythropoiesis stimulating protein. In one embodiment, said enzyme is selected a sialidase. In one embodiment said enzymatic treatment includes treatment of the erythropoiesis stimulating protein with a glycosyltransferase, in one preferred embodiment a glycosyltransferase capable of adding a terminal sugar residue to an N-linked oligosaccharide structure of the erythropoiesis stimulating protein. In one embodiment said enzymatic treatment includes treatment of the erythropoiesis stimulating proteins with a N-Acetyl-Glucosamin-transferase, in one preferred embodiment beta-1,3-N-acetyl-glucosaminyltransferase 2 (B3GNT2). In one embodiment B3GNT2 comprises an amino acid sequence of SEQ ID NO: 2. In one embodiment B3GNT2 consists of an amino acid sequence of SEQ ID NO: 2. In one embodiment said enzymatic treatment includes treatment of the erythropoiesis stimulating proteins with a galactosyltransferase, in one preferred embodiment β1,4-galactosyltransferase 1 (GalT1). In one embodiment GalT1 comprises an amino acid sequence of SEQ ID NO: 3. In one embodiment said enzymatic treatment includes treatment of the erythropoiesis stimulating proteins with a N-sialyltransferase, in one preferred embodiment α2,3-sialyltransferase (ST3) or α2,6-sialyltransferase (ST6). In one embodiment, the N-sialyltransferase is ST3.

The term enzymatically "treating" or enzymatic "treatment" means contacting the erythropoiesis stimulating protein with the respective enzyme in an aqueous solution, preferably a buffered solution.

2. Detailed Description of the Embodiments of the Invention

The invention relates to a method for the production of an in vitro glycoengineered erythropoiesis stimulating protein, comprising the steps of
  a) providing sialic acid free erythropoiesis stimulating protein,
  b) treating the erythropoiesis stimulating protein with N-Acetyl-Glucosamin-transferase B3GNT2,
  c) treating the erythropoiesis stimulating protein with galactosyltransferase,
  d) treating the erythropoiesis stimulating protein with sialyltransferase.

With the invention, recombinantly produced erythropoiesis stimulating protein is subjected to series of enzymatic treatments in order to provide an erythropoiesis stimulating protein with N-linked glycans comprising a controllable and reproducible number of poly-N-acetyl lactosamine repeats, which can assure a constant product quality and/or improve the biological function of the erythropoiesis stimulating protein. With the invention, the number of poly-N-acetyl lactosamine repeats can be increased compared to the initial erythropoiesis stimulating proteins. The series of enzymatic treatments is performed in the same order as indicated above.

In one embodiment of the invention sialic acid free erythropoiesis stimulating protein that is provided in step a) comprises a relative frequency of N-linked glycans that include a sialic acid of 5%-0%. In one embodiment of the invention sialic acid free erythropoiesis stimulating protein that is provided in step a) comprises a relative frequency of N-linked glycans that include a sialic acid of 2% to 0%. In one embodiment of the invention sialic acid free erythropoiesis stimulating protein that is provided in step a) comprises a relative frequency of N-linked glycans that include a sialic acid of 1% to 0%. In one embodiment of the invention sialic acid free erythropoiesis stimulating protein that is provided in step a) comprises a relative frequency of N-linked glycans that include a sialic acid of about 0%.

In one embodiment of the invention sialic acid free erythropoiesis stimulating protein is provided by treatment of the erythropoiesis stimulating protein with sialidase. In one embodiment sialic acid free erythropoiesis stimulating protein is provided by treatment of the erythropoiesis stimulating protein with sialidase in an aqueous solution at about 37° C. In one embodiment sialic acid free erythropoiesis stimulating protein is provided by treatment of the erythropoiesis stimulating protein with sialidase in an aqueous solution at about 37° C. for 10 to 24 hours. In one embodiment the sialidase is neuraminidase. In one embodiment the neuraminidase is of SEQ ID NO: 6. In one embodiment sialic acid free erythropoiesis stimulating protein is provided by treatment of the erythropoiesis stimulating protein with neuraminidase in an aqueous solution at 35-38° C. In one embodiment sialic acid free erythropoiesis stimulating protein is provided by treatment of the erythropoiesis stimulating protein with neuraminidase in an aqueous solution at about 37° C. In one embodiment sialic acid free erythropoiesis stimulating protein is provided by treatment of the erythropoiesis stimulating protein with neuraminidase in an aqueous solution at about 37° C. for 10 to 24 hours. In one embodiment of the invention, sialidase-treated erythropoiesis stimulating protein is purified prior to the treatment of step b).

In one embodiment the method of the invention comprises the step of providing recombinantly produced erythropoiesis stimulating protein prior to enzymatic treatment. In one preferred embodiment the method comprises the step of providing an erythropoiesis stimulating protein produced in CHO cells prior to enzymatic treatment. Methods for the production of erythropoiesis stimulating proteins in CHO cells are well known in the art (exemplarily for EPO production in CHO cells: EP0205564; EP0148605; Egrie, J C, Strickland, T W, Lane, J et al. (1986) Immunobiol. 72: 213-224; Inoue N, Takeuchi M, Ohashi H, Suzuki T (1995) Biotech Ann Rev. 1: 297-313).

In step b) of the method of the invention GlcNAc is added to the N-linked glycans of the sialic acid free erythropoiesis stimulating protein provided in step a).

In one embodiment of the method of the invention step b) is performed in an aqueous solution in presence of UDP-N-acetylglucosamine. In one embodiment of the method of the invention step b) is performed at pH 7-8, in one embodiment at about pH 7.5. In one embodiment of the method of the invention step b) is performed in presence of manganese ions and calcium ions, in one preferred embodiment in presence of $MnCl_2$ and $CaCl_2$. In one embodiment of the method of the invention step b) is performed in a Tris buffered solution of pH 7-8, in presence of NaCl, manganese ions and calcium ions. In one embodiment of the method of the invention step b) is performed in a Tris buffered solution of about pH 7.5, which comprises about 20 to 25 mM Tris, about 100 to 150 mM NaCl, and about 5 to 10 mM $MnCl_2$ and about 5 to 10 mM $CaCl_2$. In one embodiment of the method of the invention the treatment of step b) is performed for about 10 to 30 hours, in one preferred embodiment about 16 to about 24 hours. In one embodiment of the method of the invention the treatment of step b) is performed for about 10 to 30 hours at about 37° C.

In one embodiment of the method of the invention the weight ratio between the erythropoiesis stimulating protein and N-Acetyl-Glucosamin-transferase B3GNT2 in step b) is >1:1. In one embodiment of the method of the invention the weight ratio between the erythropoiesis stimulating protein and N-Acetyl-Glucosamin-transferase B3GNT2 in step b) is less than 100:1 and more than 1:1. In one embodiment of the method of the invention the weight ratio between the erythropoiesis stimulating protein and N-Acetyl-Glucosamin-transferase B3GNT2 in step b) is between 2:1 and 1:1. In one embodiment of the method of the invention the weight ratio between the erythropoiesis stimulating protein and N-Acetyl-Glucosamin-transferase B3GNT2 in step b) is about 3:2.

In one embodiment the method of the invention comprises a step of purifying the obtained erythropoiesis stimulating protein after step b) and prior to the treatment with galactosyltransferase. Thereby, the activated sugar substrate for the glycosyltransferase used in step b) is removed. Consequently, further uncontrolled addition of GlcNAc moieties to the erythropoiesis stimulating protein is avoided. This allows a controlled increase of the numbers of poly-N-acetyl lactosamine repeats.

In one embodiment of the method of the invention the step of purifying the obtained erythropoiesis stimulating protein is performed by buffer exchange into an aqueous solution of about pH 6-7, in one preferred embodiment about pH 6.5. In one embodiment the aqueous solution comprises UDP-galactose.

In one embodiment of the method of the invention the step of purifying the obtained erythropoiesis stimulating protein is performed by buffer exchange over a molecular weight cutoff filter of maximal 20 kDa into an aqueous buffer solution of about pH 6.5, wherein the buffer solution comprises about 20 mM manganese ions. In one embodiment the buffer solution comprises about 20 mM $MnCl_2$. In one embodiment the aqueous solution comprises about 20 mM manganese ions and UDP-galactose.

In step c) of the method of the invention Gal is added to the GlcNAc moieties added to the N-linked glycans in step b).

In one embodiment of the invention the treatment of the erythropoiesis stimulating protein in step c) is with galactosyltransferase GalT1. In one preferred embodiment the treatment of erythropoiesis stimulating protein in step c) is with galactosyltransferase GalT1 of SEQ ID NO. 4.

In one embodiment of the method of the invention step c) is performed using galactosyltransferase GalT1 in presence of UDP-galactose. In one embodiment of the method of the invention step c) is performed in an aqueous buffer solution of pH 6-7, in one preferred embodiment pH about 6.5, wherein the buffer solution comprises about 20 mM manganese ions, in one preferred embodiment as $MnCl_2$. In one embodiment of the method of the invention step c) is performed at about 32 to 37° C. In one embodiment of the method of the invention step c) is performed at about 32 to 37° C. for 4 to 10 hours.

In one embodiment of the method of the invention the treatment of step c) is performed for about 2 to 10 hours, in one preferred embodiment about 3 to about 5 hours.

In one embodiment of the method of the invention the weight ratio between the erythropoiesis stimulating protein and galactosyltransferase (in one embodiment GalT1) in step c) is >1:1. In one embodiment of the method of the invention the weight ratio between the erythropoiesis stimulating protein and galactosyltransferase (in one embodiment GalT1) in step c) is between 15:1 and 1:1. In one embodiment of the method of the invention the weight ratio between the erythropoiesis stimulating protein and galactosyltransferase (in one embodiment GalT1) in step c) is between 15:1 and 2:1.

In one embodiment the method of the invention comprises a step of purifying the obtained erythropoiesis stimulating protein after step c) and prior to the treatment with sialyltransferase. Thereby, the activated sugar substrate for the glycosyltransferase used in step c) is removed. Consequently, further uncontrolled addition of Gal moieties to the erythropoiesis stimulating protein is avoided. This allows a controlled increase of the numbers of poly-N-acetyl lactosamine repeats.

In one embodiment the method of the invention comprises a step of purifying the obtained erythropoiesis stimulating protein after step c) and prior to the treatment with sialyltransferase including the step of removing the galactosyltransferase (in one embodiment GalT1). In one embodiment the removal of galactosyltransferase (in one embodiment GalT1) is carried out by ion exchange chromatography. This allows a controlled increase of the numbers of poly-N-acetyl lactosamine repeats and a better substrate conversion in the subsequent sialylation step.

In one embodiment of the method of the invention the step of purifying the obtained erythropoiesis stimulating protein after step c) is performed by buffer exchange into an aqueous solution of about pH 6-7, in one preferred embodiment about pH 6.5. In one embodiment the aqueous solution comprises CMP-N-acetylneuraminic acid.

In one embodiment of the method of the invention the step of purifying the obtained erythropoiesis stimulating protein after step c) is performed by buffer exchange over a molecular weight cutoff filter of of maximal 20 kDa into an aqueous buffer solution of about pH 6.5. In one embodiment of the method of the invention the step of purifying the obtained erythropoiesis stimulating protein after step c) is performed by buffer exchange over a molecular weight cutoff filter of of maximal 20 kDa into an aqueous buffer solution of about pH 6.5 comprising CMP-N-acetylneuraminic acid.

In step d) of the method of the invention sialic acid is added to the Gal moieties added to the N-linked glycans in step c).

In one embodiment of the method of the invention the treatment of erythropoiesis stimulating protein in step d) is with sialyltransferase ST3. In one preferred embodiment the treatment of erythropoiesis stimulating protein in step d) is with sialyltransferase ST3 of SEQ ID NO: 4. This allows generation of a erythropoiesis stimulating protein with a high relative frequency of alpha-2,3-sialylated N-glycans. The high relative frequency of sialylated N-glycans may additionally contribute to a higher specific bioactivity and a higher serum half life of the erythropoiesis stimulating protein.

In one embodiment of the method of the invention, in one embodiment a method using sialyltransferase ST3 as indicated above, step d) is performed in presence of CMP-N-acetylneuraminic acid. In one embodiment of the method of the invention step d) is performed in an aqueous buffer solution of pH 6-7, in one preferred embodiment pH about 6.5. In one embodiment of the method of the invention step d) is performed for 10 to 20 hours, in one preferred embodiment for about 16 to about 18 hours. In one embodiment of the method of the invention step d) is performed for 10 to 20 hours, in one preferred embodiment for about 16 to about 18 hours at about 37° C.

In one embodiment of the method of the invention the weight ratio between erythropoiesis stimulating protein and sialyltransferase (in one embodiment ST3) in step d) is >1:1. In one embodiment of the method of the invention the weight ratio between erythropoiesis stimulating protein and sialyltransferase (in one embodiment ST3) in step d) is between >1:1 and 50:1. In one embodiment of the method of the invention the weight ratio between erythropoiesis stimulating protein and sialyltransferase (in one embodiment ST3) in step d) is between 2:1 and 50:1.

In one embodiment of the invention the treatment of erythropoiesis stimulating protein in step d) is with sialyltransferase ST6. In one preferred embodiment the treatment of erythropoiesis stimulating protein in step d) is with sialyltransferase ST6 of SEQ ID NO: 5.

The invention also relates to the use of the method of the invention for increasing the number of poly-N-acetyl lactosamine repeats on N-glycans of an erythropoiesis stimulating protein.

Another aspect of the invention is the method of the invention for increasing the number of poly-N-acetyl lactosamine repeats on N-glycans of an erythropoiesis stimulating protein.

Another aspect of the invention is the use of the method of the invention for providing an erythropoiesis stimulating protein with a controlled number of poly-N-acetyl lactosamine repeats on N-glycans of the erythropoiesis stimulating protein. In one embodiment the method is used for providing erythropoiesis stimulating protein with up to 15 poly-N-acetyl lactosamine repeats per N-glycosylation site. In one embodiment the method is used for providing erythropoiesis stimulating protein with 2-15 poly-N-acetyl lactosamine repeats per N-glycosylation site. In one embodiment the method is used for providing erythropoiesis stimulating protein with 2-12 poly-N-acetyl lactosamine repeats per N-glycosylation site. In one embodiment the method is used for providing erythropoiesis stimulating protein with 4-10 poly-N-acetyl lactosamine repeats per N-glycosylation site.

In one embodiment the method is used for providing erythropoiesis stimulating protein with up to 15 poly-N-acetyl lactosamine repeats per erythropoiesis stimulating protein. In one embodiment the method is used for providing erythropoiesis stimulating protein with 2-15 poly-N-acetyl lactosamine repeats per erythropoiesis stimulating protein.

Another aspect of the invention is the use of the method of the invention for improving the specific activity of the erythropoiesis stimulating protein.

Another aspect of the invention is an in vitro glycoengineered erythropoiesis stimulating protein produced by a method of the invention.

Another aspect of the invention is a population of erythropoiesis stimulating proteins, characterized in that the relative frequency of N-linked glycans comprising more than two poly-N-acetyl lactosamine repeats on each N-glycosylation site is more than 90%, in one embodiment more than 99%, in one embodiment about 100%, in one embodiment exactly 100%.

Within the population of erythropoiesis stimulating proteins of the invention all erythropoiesis stimulating proteins comprise 2 or more poly-N-acetyl lactosamine repeats. Consequently, the population of erythropoiesis stimulating proteins of the invention is free of erythropoiesis stimulating proteins with zero or one poly-N-acetyl lactosamine repeats. In this connection, "free" (of erythropoiesis stimulating proteins with zero or one poly-N-acetyl lactosamine repeats) refers to a fraction of 0.1% and less, in one embodiment to a fraction of 0%. The term "fraction" in this refers to the number of molecules in the sample, e.g. a fraction of 1% means one erythropoiesis stimulating protein out of 100 erythropoiesis stimulating protein molecules.

Another aspect of the invention is a population of erythropoiesis stimulating proteins, characterized in that the average number of poly-N-acetyl lactosamine repeats per individual erythropoiesis stimulating protein is at least 10. In one embodiment the average number of poly-N-acetyl lactosamine repeats per erythropoiesis stimulating protein is 10 to 40.

In one embodiment, the population of erythropoiesis stimulating proteins of the invention is characterized in that the relative frequency of N-linked glycans comprising more than two poly-N-acetyl lactosamine repeats on each N-glycosylation site is more than 99%, in one embodiment about 100%, in one embodiment exactly 100%; and the average number of poly-N-acetyl lactosamine repeats per erythropoiesis stimulating protein is more than 10, in one embodiment 10 to 40. In one embodiment the average number of poly-N-acetyl lactosamine repeats per N-glycosylation site is at least 2. In one embodiment the average number of poly-N-acetyl lactosamine repeats per N-glycosylation site is at least 3.

In one embodiment the population of erythropoiesis stimulating proteins is produced by a method of the invention.

3. Specific Embodiments of the Invention

In the following specific embodiments of the invention are listed.
1. A method for the production of in vitro glycoengineered erythropoiesis stimulating protein, comprising the steps of
    a) providing sialic acid free erythropoiesis stimulating protein,
    b) treating the erythropoiesis stimulating protein with N-Acetyl-Glucosamin-transferase B3GNT2,
    c) treating the erythropoiesis stimulating protein with galactosyltransferase,
    d) treating the erythropoiesis stimulating protein with sialyltransferase.
2. The method of embodiment 1, wherein the erythropoiesis stimulating protein is erythropoietin.
3. The method of any one of the preceding embodiments, characterized in that step b) is performed in an aqueous solution in presence of UDP-N-acetylglucosamine.
4. The method of any one of the preceding embodiments, characterized in that step b) is performed at pH 7-8.
5. The method of any one of the preceding embodiments, characterized in that step b) is performed at about pH 7.5.
6. The method of any one of the preceding embodiments, characterized in that step b) is performed in presence of manganese ions and calcium ions.

7. The method of any one of the preceding embodiments, characterized in that step b) is performed in presence of MnCl$_2$ and CaCl$_2$.
8. The method of one of embodiments 1 to 4, characterized in that step b) is performed in a Tris buffered solution of pH 7-8, in presence of NaCl, manganese ions and calcium ions.
9. The method of any one of the preceding embodiments, characterized in that step b) is performed in a Tris buffered solution of about pH 7.5, which comprises about 25 mM Tris, about 150 mM NaCl, and about 10 mM MnCl$_2$ and about 10 mM CaCl$_2$.
10. The method of any one of the preceding embodiments, wherein the treatment of step b) is performed for about 10 to 30 hours,
11. The method of any one of the preceding embodiments, wherein the treatment of step b) is performed for about 16 to about 24 hours.
12. The method of any one of the preceding embodiments, wherein the treatment of step b) is performed at about 37° C.
13. The method of any one of the preceding embodiments, the weight ratio between erythropoiesis stimulating protein and N-Acetyl-Glucosamin-transferase B3GNT2 in step b) is >1:1.
14. The method of any one of the preceding embodiments, characterized in that the method comprises a step of purifying the obtained erythropoiesis stimulating protein after step b) and prior to the treatment with galactosyltransferase.
15. The method of embodiment 14, wherein the step of purifying the obtained erythropoiesis stimulating protein is performed by buffer exchange into an aqueous solution of about pH 6-7
16. The method of embodiment 14, wherein the step of purifying the obtained erythropoiesis stimulating protein is performed by buffer exchange into an aqueous solution of about pH 6.5.
17. The method of one of embodiments 14 to 16, wherein the step of purifying the obtained erythropoiesis stimulating protein is performed by buffer exchange over a molecular weight cutoff filter of of maximal 20 kDa into an aqueous buffer solution of about pH 6.5, wherein the buffer solution comprises about 20 mM manganese ions.
18. The method of embodiment 17, wherein the buffer solution comprises about 20 mM MnCl$_2$.
19. The method of embodiment 17 or 18, wherein the buffer solution comprises UDP-galactose.
20. The method of any one of the preceding embodiments, characterized in that step c) is performed using galactosyltransferase GalT1 in presence of UDP-galactose.
21. The method of embodiment 20, characterized in that step c) is performed in an aqueous buffer solution of pH 6-7, wherein the buffer solution comprises mangangese ions.
22. The method of embodiment 21, wherein the buffer solution has a pH of about 6.5.
23. The method of embodiments 21 or 22, wherein the buffer solution comprises 20 mM mangangese ions.
24. The method of one of embodiments 21 to 23, wherein the buffer solution comprises MnCl$_2$.
25. The method of one of embodiments 20 to 24, wherein the treatment of step c) is performed for about 2 to 10 hours
26. The method of one of embodiments 20 to 24, wherein the treatment of step c) is performed for about 3 to about 5 hours.
27. The method of one of embodiments 20 to 26, wherein the weight ratio between erythropoiesis stimulating protein and galactosyltransferase in step c) is >1:1.
28. The method of any one of the preceding embodiments, characterized in that the method comprises a step of purifying the obtained erythropoiesis stimulating protein after step c) and prior to the treatment with sialyltransferase.
29. The method of embodiment 28, wherein the step of purifying the obtained erythropoiesis stimulating protein is performed by buffer exchange into an aqueous solution of about pH 6-7.
30. The method of embodiment 28, wherein the step of purifying the obtained erythropoiesis stimulating protein is performed by buffer exchange into an aqueous solution of about pH 6.5.
31. The method of one of embodiments 28 to 30, wherein step of purifying the obtained erythropoiesis stimulating protein is performed by buffer exchange over a molecular weight cutoff filter of of maximal 20 kDa into an aqueous buffer solution of about pH 6.5.
32. The method of one of embodiments 29 to 31, wherein the aqueous solution comprises CMP-N-acetylneuraminic acid.
33. The method of any one of the preceding embodiments, characterized in that step d) is performed using sialyltransferase ST3.
34. The method of embodiment 33, characterized in that step d) is performed in presence of CMP-N-acetylneuraminic acid.
35. The method of embodiment 33 or 34, wherein step d) is performed in an aqueous buffer solution of pH 6-7.
36. The method of embodiment 33 or 34, wherein step d) is performed in an aqueous buffer solution of about pH 6.5.
37. The method of one of embodiments 33 to 36, wherein step d) is performed for 10 to 20 hours.
38. The method of one of embodiments 33 to 36, wherein step d) is performed for about 16 to about 18 hours.
39. The method of one of embodiments 33 to 38, wherein step d) is performed at about 37° C.
40. The method of one of embodiments 33 to 39, wherein invention the weight ratio between erythropoiesis stimulating protein and sialyltransferase in step d) is >1:1.
41. The method of any one of the preceding embodiments, wherein the sialic acid free erythropoiesis stimulating protein comprises a relative frequency of N-linked glycans that include a sialic acid of 5-0%.
42. The method of any one of the preceding embodiments, wherein the sialic acid free erythropoiesis stimulating protein comprises a relative frequency of N-linked glycans that include a sialic acid of 2%-0%.
43. The method of any one of the preceding embodiments, wherein the sialic acid free erythropoiesis stimulating protein comprises a relative frequency of N-linked glycans that include a sialic acid of 1-0%.
44. The method of any one of the preceding embodiments, wherein the sialic acid free erythropoiesis stimulating protein comprises a relative frequency of N-linked glycans that include a sialic acid of about 0%.
45. The method of any one of the preceding embodiments, characterized in that sialic acid free erythropoiesis stimulating protein is provided by treatment of erythropoiesis stimulating protein with sialidase.
46. The method of any one of the preceding embodiments, comprising the step of providing erythropoiesis stimulating protein produced in CHO cells prior to enzymatic treatment.

47. Use of the method of any one of the preceding embodiments for increasing the number of poly-N-acetyl lactosamine repeats on the N-glycans of the erythropoiesis stimulating protein.
48. Use of the method of one of embodiments 1 to 46 for providing an erythropoiesis stimulating protein with a controlled number of poly-N-acetyl lactosamine repeats on their N-glycans.
49. Use of the method of one of embodiments 1 to 46 for providing erythropoiesis stimulating protein with up to 15 poly-N-acetyl lactosamine repeats per N-glycosylation site.
50. The use of embodiment 49 for providing erythropoiesis stimulating protein with 2 or more poly-N-acetyl lactosamine repeats per N-glycosylation site.
51. Use of the method of one of embodiments 1 to 46 for improving the specific activity of the erythropoiesis stimulating protein.
52. In vitro glycoengineered erythropoiesis stimulating protein produced by a method of any one of embodiments 1 to 46.
53. In vitro glycoengineered erythropoietin produced by a method of any one of embodiments 1 to 46.
54. A population of erythropoiesis stimulating proteins, characterized in that the relative frequency of N-linked glycans comprising more than two poly-N-acetyl lactosamine repeats on each N-glycosylation site is more than 90%.
55. The population of erythropoiesis stimulating proteins of embodiment 54, wherein the relative frequency of N-linked glycans comprising more than two poly-N-acetyl lactosamine repeats on each N-glycosylation site is more than 99%.
56. The population of erythropoiesis stimulating proteins of embodiment 54, wherein the relative frequency of N-linked glycans comprising more than two poly-N-acetyl lactosamine repeats on each N-glycosylation site is about 100%.
57. The population of erythropoiesis stimulating protein proteins of embodiment 54, wherein the relative frequency of N-linked glycans comprising more than two poly-N-acetyl lactosamine repeats on each N-glycosylation site is exactly 100%.
58. The population of erythropoiesis stimulating proteins of one of embodiments 54 to 57, wherein the population of erythropoiesis stimulating proteins is free of erythropoiesis stimulating proteins with zero or one poly-N-acetyl lactosamine repeats.
59. The population of erythropoiesis stimulating proteins of one of embodiments 54 to 57, wherein the population of erythropoiesis stimulating proteins comprises a fraction of 0.1% and less of erythropoiesis stimulating proteins with zero or one poly-N-acetyl lactosamine repeats.
60. The population of erythropoiesis stimulating proteins of one of embodiments 54 to 57, wherein the population of erythropoiesis stimulating proteins comprises a fraction of 0% of erythropoiesis stimulating proteins with zero or one poly-N-acetyl lactosamine repeats.
61. The population of erythropoiesis stimulating proteins of one of embodiments 54 to 60, wherein that the average number of poly-N-acetyl lactosamine repeats per individual erythropoiesis stimulating protein is at least 4.
62. The population of erythropoiesis stimulating proteins of one of embodiments 54 to 60, wherein that the average number of poly-N-acetyl lactosamine repeats per individual erythropoiesis stimulating protein is at least 10.
63. The population of erythropoiesis stimulating proteins of one of embodiments 54 to 62, wherein that the average number of poly-N-acetyl lactosamine repeats per individual erythropoiesis stimulating protein is up to 40.
64. The population of erythropoiesis stimulating proteins of one of embodiments 54 to 63, wherein the erythropoiesis stimulating protein is erythropoietin.

Description of the Amino Acid Sequences erythropoietin 165 aa

SEQ ID NO: 1

```
APPRLICDSRVLERYLLEAKEAENITTGCAEHCSLNENITVPDTKVNFYAW
KRMEVGQQAVEVWQGLALLSEAVLRGQALLVNSSQPWEPLQLHVDKAVSGL
RSLTTLLRALGAQKEAISPPDAASAAPLRTITADTFRKLFRVYSNFLRGKL
KLYTGEACRTGD
```

N-Acetyl-Glucosamin-transferase B3GNT2

SEQ ID NO: 2

```
MVSRSLVGILMMANVFIYFIMEVSKSSSQEKNGKGEVIIPKEKFWKISTPP
EAYWNREQEKLNRQYNPILSMLTNQTGEAGRLSNISHLNYCEPDLRVTSVV
TGFNNLPDRFKDFLLYLRCRNYSLLIDQPDKCAKKPFLLLAIKSLTPHFAR
RQAIRESWGQESNAGNQTVVRVFLLGQTPPEDNHPDLSDMLKFESEKHQDI
LMWNYRDTFFNLSLKEVLFLRWVSTSCPDTEFVFKGDDDVFVNTHHILNYL
NSLSKTKAKDLFIGDVIHNAGPHRDKKLKYYIPEVVYSGLYPPYAGGGGFL
YSGHLALRLYHITDQVHLYPIDDVYTGMCLQKLGLVPEKHKGFRTFDIEEK
NKNNICSYVDLMLVHSRKPQEMIDIWSQLQSAHLKC
``` galactosyltransferase GalT1

SEQ ID NO: 3

```
MGVHECPAWLWLLLSLLSLPLGLPVLGAPRDLSRLPQLVGVSTPLQGGSNS
AAAIGQSSGELRTGGARPPPPLGASSQPRPGGDSSPVVDSGPGPASNLTSV
PVPHTTALSLPACPEESPLLVGPMLIEFNMPVDLELVAKQNPNVKMGGRYA
PRDCVSPHKVAIIIPFRNRQEHLKYWLYYLHPVLQRQQLDYGIYVINQAGD
TIFNRAKLLNVGFQEALKDYDYTCFVFSDVDLIPMNDHNAYRCFSQPRHIS
VAMDKFGFSLPYVQYFGGVSALSKQQFLTINGFPNNYWGWGGEDDDIFNRL
VFRGMSISRPNAVVGRCRMIRHSRDKKNEPNPQRFDRIAHTKETMLSDGLN
SLTYQVLDVQRYPLYTQITVDIGTPS
``` human α2,3-sialyltransferase (ST3)

SEQ ID NO: 4

```
MGVHECPAWLWLLLSLLSLPLGLPVLGVAPVEMKRRNKIQPCLSKPAFASL
LRFHQFHPFLCAADFRKIASLYGSDKFDLPYGMRTSAEYFRLALSKLQSCD
LFDEFDNIPCKKCVVVGNGGVLKNKTLGEKIDSYDVIIRMNNGPVLGHEEE
VGRRTTFRLFYPESVFSDPIHNDPNTTVILTAFKPHDLRWLLELLMGDKIN
TNGFWKKPALNLIYKPYQIRILDPFIIRTAAYELLHFPKVFPKNQKPKHPT
TGIIAITLAFYICHEVHLAGFKYNFSDLKSPLHYYGNATMSLMNKNAYHNV
TAEQLFLKDIIEKNLVINLTQD
``` human α2,6-sialyltransferase (ST6)

SEQ ID NO: 5

```
MGVHECPAWLWLLLSLLSLPLGLPVLGAPEASFQVWNKDSSSKNLIPRLQK
IWKNYLSMNKYKVSYKGPGPGIKFSAEALRCHLRDHVNVSMVEVTDFPFNT
```

-continued

SEWEGYLPKESIRTKAGPWGRCAVVSSAGSLKSSQLGREIDDHDAVLRFNG

APTANFQQDVGIKTTIRLMNSQLVTTEKRFLKDSLYNEGILIVWDPSVYHS

DIPKWYQNPDYNFFNNYKTYRKLHPNQPFYILKPQMPWELWDILQEISPEE

IQPNPPSSGMLGIIIMMTLCDQVDIYEFLPSKRKTDVCYYYQKFFDSACTM

GAYHPLLYEKNLVKHLNQGTDEDIYLLGKATLPGFRTIHC neuraminidase from Clostridium perfringens
SEQ ID NO: 6
MCNKNNTFEKNLDISHKPEPLILFNKDNNIWNSKYFRIPNIQLLNDGTILT

FSDIRYNGPDDHAYIDIASARSTDFGKTWSYNIAMKNNRIDSTYSRVMDST

TVITNTGRIILIAGSWNINGNWAMTTSTRRSDWSVQMIYSDDNGLTWSNKI

DLTKDSSKVKNQPSNTIGWLGGVGSGIVMDDGTIVMPAQISLRENNENNYY

SLIIYSKDNGETWTMGNKVPNSNTSENMVIELDGALIMSTRYDYSGYRAAY

ISHDLGTTWEIYEPLNGKILTGKGSGCQGSFIKATTSNGHRIGLISAPKNT

KGEYIRDNIAVYMIDFDDLSKGVQEICIPYPEDGNKLGGGYSCLSFKNNHL

GIVYEANGNIEYQDLTPYYSLINKQ

EXAMPLES

The following examples are provided to aid the understanding of the present invention, the true scope of which is set forth in the appended claims. It is understood that modifications can be made in the procedures set forth without departing from the spirit of the invention.

Example 1

Increase of Number of Poly-N-Acetyl Lactosamine Repeats by In Vitro Glycoengineering of EPO (No Purification Between B3Gnt2 and GalT1 Treatments)

Erythropoietin (EPO) was provided by recombinant production in CHO cells (see also EP0205564; EP0148605).

In vitro glycoengineering (IVGE) treatment of the recombinant EPO was performed as follows:

EPO was desialylated by incubation with neuraminidase (Roche) in aqueous buffered solution of pH 7.5 at 37° C. for 18 hours.

For addition of GlcNAc moieties to the N-linked glycans 1.5 mg desialylated erythropoietin were mixed with 1.0 mg N-acetylglucosamine transferase, B3GnT2 (dissolved in 25 mM Tris, 150 mM NaCl, pH7.5). 8.8 mg UDP-N-acetylglucosamine, 2.5 mg $MnCl_2$ and 2.2 mg $CaCl_2$ (each dissolved in water) were added to the solution. The sample was incubated at 37° C. for 24 hours.

Subsequently for addition of Gal moieties to the N-linked glycans 149 μg galactosyltransferase, GalT1 and 3 mg UDP-galactose were added, followed by incubation at 37° C. for 5 hours.

Finally, 54 μg sialyltransferase, ST3, 70 mg CMP-N-acetyl-neuraminic acid, 17 μg alkaline phosphatase and 20 μl of 10 mM $ZnCl_2$ solution were added and incubated at 37° C. for 18 hours.

The analysis of glycostructures present on the N-linked glycans of the obtained in vitro glycoengineered erythropoietin was performed by LCMS peptide mapping after endoproteinase Glu-C digest. For this, 250 μg sample were denatured (using guanidinium hydrochloride), reduced (using dithiothreitol), carboxymethylated (using iodoacetic acid) and finally digested by endoproteinase Glu-C. The digest was analyzed by RP-UHPLC with an online coupled mass spectrometer. Resulting data sets were evaluated for specific glycan signal of the peptides bearing the N-glycosylation sites (asparagine 24, 38 and 83).

Results are shown in the following tables comparing recombinantly produced erythropoietin that was not treated with any glycosidase or glycosyltransferase ("EPO before IVGE") and erythropoietin resulting from a method of the invention as described before ("EPO after IVGE"). The term "repeat" refers to the poly N-acetyl lactosamine repeat as defined above.

TABLE 1

EPO before IVGE (comparative data)
Indicated is the fraction of erythropoietin glycoproteins comprising 0, 1, 2 or more than 2 poly N-acelyl lactosamine repeats at the respective N-glycan present at the indicated N-glycosylation site.

| | 0 repeats [%] | 1 repeat [%] | 2 repeats [%] | >2 repeats [%] |
|---|---|---|---|---|
| Asn 24 | 76 | 18 | 6 | 0 |
| Asn 38 | 66 | 27 | 7 | 0 |
| Asn 83 | 64 | 28 | 8 | 0 |

TABLE 2

| EPO before IVGE (comparative data) | |
|---|---|
| average number of repeats per EPO molecule: | ~1 |
| fraction of EPO molecules with 1 and less repeats: | 79% |
| fraction of EPO molecules with 2 and more repeats: | 21% |

TABLE 3

EPO after IVGE
Indicated is the fraction of erythropoietin glycoproteins comprising 0, 1, 2 or more than 2 poly N-acelyl lactosamine repeats at the respective N-glycan present at the indicated N-glycosylation site.

| | 0 repeats [%] | 1 repeat [%] | 2 repeats [%] | >2 repeats [%] |
|---|---|---|---|---|
| Asn 24 | 0 | 0 | 0 | 100 |
| Asn 38 | 0 | 0 | 0 | 100 |
| Asn 83 | 0 | 0 | 0 | 100 |

TABLE 4

EPO after IVGE
Indicated is the minimal number and the range of the number of poly N-acetyl lactosamine repeats at the respective N-glycan present at the indicated N-glycosylation site.

| | minimal # repeats | range of # of repeats |
|---|---|---|
| Asn 24 | 4 | 4-12 |
| Asn 38 | 8 | 8-13 |
| Asn 83 | 8 | 8-12 |

TABLE 5

| EPO after IVGE | |
|---|---|
| average number of repeats per EPO molecule: | ≥20 |
| fraction of EPO molecules with 1 and less repeats: | 0% |
| fraction of EPO molecules with 2 and more repeats: | 100% |

The results indicate that the IVGE procedure results in a population of EPO molecules, wherein all individual EPO molecules comprise several poly N-acetyl lactosamine repeat on each N-glycosylation site. All EPO molecules comprise at least 20 poly N-acetyl lactosamine repeats per molecule.

Untreated CHO produced EPO comprises a fraction of 79% of individual molecules with zero or one poly N-acetyl lactosamine repeats per EPO molecule.

Example 2

Controlled Number of Poly-N-Acetyl Lactosamine Repeats by In Vitro Glycoengineering of EPO (Purification Steps Between B3Gnt2 and GalT1 Treatment and Between GalT1 and ST3 Treatment)

Erythropoietin (EPO) was provided by recombinant production in CHO cells as in Example 1.

In vitro glycoengineering (IVGE) treatment of the recombinant EPO was performed as follows:

EPO was desialylated as described in Example 1.

For addition of GlcNAc moieties to the N-linked glycans 90 μg of the desialylated erythropoietin glycoproteins were mixed with 60 μg N-acetylglucosamine transferase B3GnT2 (dissolved in 25 mM Tris, 150 mM NaCl, pH7.5), and 525 μg UDP-N-acetylglucosamine in 25 mM Tris buffer including 10 mM $CaCl_2$ and 10 mM $MnCl_2$ at pH 7.5. The sample was incubated at 37° C. for 16 hours. One third of the sample containing EPO glycoproteins was used for analytical purposes.

Residual material of the EPO glycoproteins was purified by buffer exchange to 100 mM MES buffer including 20 mM $MnCl_2$ and 20 mM UDP-galactose at pH 6.5 using Vivaspin centrifugation columns (10 kD filter).

For addition of Gal moieties to the N-linked glycans 27 μg galactosyltransferase, GalT1, was added to the EPO glycoproteins sample, which was subsequently incubated at 32° C. for 4 hours. Subsequently, half of the material was used for analytical purposes.

Residual material of the EPO glycoproteins was purified by buffer exchange to 100 mM MES, pH6.5, incl. 150 mg/ml CMP-N-acetyl-neuraminic acid. 27 μg sialyltransferase, ST3, were added followed by incubation at 37° C. for 16 hours.

The analysis of glycostructures present on the N-linked glycans of the obtained in vitro glycoengineered erythropoietin was performed by mass spectrometry. For this, samples were injected in a UHPLC system without further sample preparation. The UHPLC system was coupled to a mass spectrometer. Data sets (deconvoluted sum spectra) were evaluated with regard to glycan specific signals.

Results are shown in the following data sets comparing recombinantly produced erythropoietin that was not treated with any glycosidase or glycosyltransferase ("EPO before IVGE") and erythropoietin resulting from a method of the invention as described before ("EPO after IVGE"). The term "repeat" refers to the poly N-acetyl lactosamine repeat as defined above.

TABLE 6

| EPO before IVGE (comparative data) | |
|---|---|
| average number of repeats per EPO molecule: | ~1 |
| fraction of EPO molecules with 1 and less repeats: | 80% |
| fraction of EPO molecules with 2 and more repeats: | 20% |

TABLE 7

| EPO after IVGE | |
|---|---|
| average number of repeats per EPO molecule: | ≥12 |
| fraction of EPO molecules with 1 and less repeats: | 0% |
| fraction of EPO molecules with 2 and more repeats: | 100% |

Untreated CHO produced EPO comprised a fraction of 80% of individual molecules with zero or one poly N-acetyl lactosamine repeats per EPO molecule, while in vitro glycoengineered EPO comprised 100% of EPO glycoproteins with 2 and more poly N-acetyl lactosamine repeats. The average number of poly N-acetyl lactosamine repeats per EPO glycoprotein is 12 and more, whereas untreated CHO produced EPO comprised about 1 poly N-acetyl lactosamine repeat per EPO glycoprotein.

The invention claimed is:

1. An in vitro glycoengineered erythropoietin wherein the average number of poly-N-acetyl lactosamine repeats per erythropoietin is 10 to 40 produced by a method comprising the steps of
   a) treating erythropoietin with sialidase to obtain erythropoietin comprising N-linked glycans that include a sialic acid at a relative frequency of 1% to about 0%,
   b) treating the erythropoietin provided in step a) with beta-1,3-N-acetylglucosaminyltransferase 2 (B3GNT2),
   c) treating the erythropoietin obtained in step b) with galactosyltransferase, and
   d) treating the erythropoietin obtained in step c) with sialyltransferase.

2. The in vitro glycoengineered erythropoietin of claim 1, characterized in that step b) is performed in presence of manganese ions and calcium ions.

3. The in vitro glycoengineered erythropoietin of claim 1, wherein the weight ratio between erythropoietin and B3GNT2 in step b) is between 2:1 and 1:1.

4. The in vitro glycoengineered erythropoietin of claim 1, characterized in that the method comprises a step of purifying the obtained erythropoietin after step b) and prior to the treatment with galactosyltransferase.

5. The in vitro glycoengineered erythropoietin of claim 1, characterized in that step c) is performed using galactosyltransferase GalT1 in presence of UDP-galactose.

6. The in vitro glycoengineered erythropoietin of claim 1, characterized in that the method comprises a step of purifying the obtained erythropoietin after step c) and prior to the treatment with sialyltransferase.

7. The in vitro glycoengineered erythropoietin of claim 1, characterized in that step d) is performed using sialyltransferase ST3.

8. A population of erythropoietin, characterized in that the relative frequency of N-linked glycans comprising more than two poly-N-acetyl lactosamine repeats on each N-glycosylation site is more than 90%, and characterized in that the average number of poly-N-acetyl lactosamine repeats per erythropoietins is 10 to 40.

9. The population of erythropoietins of claim 8, wherein the population of erythropoietins is free of erythropoietins with zero or one poly-N-acetyl lactosamine repeats.

* * * * *

SEQUENCE LISTING

```
<160> NUMBER OF SEQ ID NOS: 6

<210> SEQ ID NO 1
<211> LENGTH: 165
<212> TYPE: PRT
<213> ORGANISM: Homo sapiens

<400> SEQUENCE: 1

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
```

```
                    85                  90                  95
Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
                115                 120                 125

Pro Leu Arg Thr Ile Thr Ala Asp Thr Phe Arg Lys Leu Phe Arg Val
                130                 135                 140

Tyr Ser Asn Phe Leu Arg Gly Lys Leu Lys Leu Tyr Thr Gly Glu Ala
145                 150                 155                 160

Cys Arg Thr Gly Asp
                165

<210> SEQ ID NO 2
<211> LENGTH: 393
<212> TYPE: PRT
<213> ORGANISM: Homo sapiens

<400> SEQUENCE: 2

Met Val Ser Arg Ser Leu Val Gly Ile Leu Met Met Ala Asn Val Phe
1               5                   10                  15

Ile Tyr Phe Ile Met Glu Val Ser Lys Ser Ser Ser Gln Glu Lys Asn
                20                  25                  30

Gly Lys Gly Glu Val Ile Ile Pro Lys Glu Lys Phe Trp Lys Ile Ser
                35                  40                  45

Thr Pro Pro Glu Ala Tyr Trp Asn Arg Glu Gln Glu Lys Leu Asn Arg
            50                  55                  60

Gln Tyr Asn Pro Ile Leu Ser Met Leu Thr Asn Gln Thr Gly Glu Ala
65                  70                  75                  80

Gly Arg Leu Ser Asn Ile Ser His Leu Asn Tyr Cys Glu Pro Asp Leu
                85                  90                  95

Arg Val Thr Ser Val Val Thr Gly Phe Asn Asn Leu Pro Asp Arg Phe
                100                 105                 110

Lys Asp Phe Leu Leu Tyr Leu Arg Cys Arg Asn Tyr Ser Leu Leu Ile
                115                 120                 125

Asp Gln Pro Asp Lys Cys Ala Lys Lys Pro Phe Leu Leu Leu Ala Ile
                130                 135                 140

Lys Ser Leu Thr Pro His Phe Ala Arg Arg Gln Ala Ile Arg Glu Ser
145                 150                 155                 160

Trp Gly Gln Glu Ser Asn Ala Gly Asn Gln Thr Val Val Arg Val Phe
                165                 170                 175

Leu Leu Gly Gln Thr Pro Pro Glu Asp Asn His Pro Asp Leu Ser Asp
                180                 185                 190

Met Leu Lys Phe Glu Ser Glu Lys His Gln Asp Ile Leu Met Trp Asn
                195                 200                 205

Tyr Arg Asp Thr Phe Phe Asn Leu Ser Leu Lys Glu Val Leu Phe Leu
                210                 215                 220

Arg Trp Val Ser Thr Ser Cys Pro Asp Thr Glu Phe Val Phe Lys Gly
225                 230                 235                 240

Asp Asp Asp Val Phe Val Asn Thr His His Ile Leu Asn Tyr Leu Asn
                245                 250                 255

Ser Leu Ser Lys Thr Lys Ala Lys Asp Leu Phe Ile Gly Asp Val Ile
                260                 265                 270

His Asn Ala Gly Pro His Arg Asp Lys Lys Leu Lys Tyr Tyr Ile Pro
                275                 280                 285
```

```
Glu Val Val Tyr Ser Gly Leu Tyr Pro Pro Tyr Ala Gly Gly Gly
    290                 295                 300

Phe Leu Tyr Ser Gly His Leu Ala Leu Arg Leu Tyr His Ile Thr Asp
305                 310                 315                 320

Gln Val His Leu Tyr Pro Ile Asp Asp Val Tyr Thr Gly Met Cys Leu
                325                 330                 335

Gln Lys Leu Gly Leu Val Pro Glu Lys His Lys Gly Phe Arg Thr Phe
                340                 345                 350

Asp Ile Glu Glu Lys Asn Lys Asn Ile Cys Ser Tyr Val Asp Leu
                355                 360                 365

Met Leu Val His Ser Arg Lys Pro Gln Glu Met Ile Asp Ile Trp Ser
370                 375                 380

Gln Leu Gln Ser Ala His Leu Lys Cys
385                 390

<210> SEQ ID NO 3
<211> LENGTH: 383
<212> TYPE: PRT
<213> ORGANISM: Arabidopsis thaliana

<400> SEQUENCE: 3

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Arg Asp Leu
                20                  25                  30

Ser Arg Leu Pro Gln Leu Val Gly Val Ser Thr Pro Leu Gln Gly Gly
            35                  40                  45

Ser Asn Ser Ala Ala Ala Ile Gly Gln Ser Ser Gly Glu Leu Arg Thr
50                  55                  60

Gly Gly Ala Arg Pro Pro Pro Leu Gly Ala Ser Ser Gln Pro Arg
65                  70                  75                  80

Pro Gly Gly Asp Ser Ser Pro Val Val Asp Ser Gly Pro Gly Pro Ala
                85                  90                  95

Ser Asn Leu Thr Ser Val Pro Val Pro His Thr Thr Ala Leu Ser Leu
                100                 105                 110

Pro Ala Cys Pro Glu Glu Ser Pro Leu Leu Val Gly Pro Met Leu Ile
            115                 120                 125

Glu Phe Asn Met Pro Val Asp Leu Glu Leu Val Ala Lys Gln Asn Pro
130                 135                 140

Asn Val Lys Met Gly Gly Arg Tyr Ala Pro Arg Asp Cys Val Ser Pro
145                 150                 155                 160

His Lys Val Ala Ile Ile Pro Phe Arg Asn Arg Gln Glu His Leu
                165                 170                 175

Lys Tyr Trp Leu Tyr Tyr Leu His Pro Val Leu Gln Arg Gln Leu
                180                 185                 190

Asp Tyr Gly Ile Tyr Val Ile Asn Gln Ala Gly Asp Thr Ile Phe Asn
                195                 200                 205

Arg Ala Lys Leu Leu Asn Val Gly Phe Gln Glu Ala Leu Lys Asp Tyr
210                 215                 220

Asp Tyr Thr Cys Phe Val Phe Ser Asp Val Asp Leu Ile Pro Met Asn
225                 230                 235                 240

Asp His Asn Ala Tyr Arg Cys Phe Ser Gln Pro Arg His Ile Ser Val
                245                 250                 255

Ala Met Asp Lys Phe Gly Phe Ser Leu Pro Tyr Val Gln Tyr Phe Gly
                260                 265                 270
```

```
Gly Val Ser Ala Leu Ser Lys Gln Gln Phe Leu Thr Ile Asn Gly Phe
            275                 280                 285

Pro Asn Asn Tyr Trp Gly Trp Gly Gly Glu Asp Asp Asp Ile Phe Asn
            290                 295                 300

Arg Leu Val Phe Arg Gly Met Ser Ile Ser Arg Pro Asn Ala Val Val
305                 310                 315                 320

Gly Arg Cys Arg Met Ile Arg His Ser Arg Asp Lys Lys Asn Glu Pro
            325                 330                 335

Asn Pro Gln Arg Phe Asp Arg Ile Ala His Thr Lys Glu Thr Met Leu
            340                 345                 350

Ser Asp Gly Leu Asn Ser Leu Thr Tyr Gln Val Leu Asp Val Gln Arg
            355                 360                 365

Tyr Pro Leu Tyr Thr Gln Ile Thr Val Asp Ile Gly Thr Pro Ser
            370                 375                 380

<210> SEQ ID NO 4
<211> LENGTH: 328
<212> TYPE: PRT
<213> ORGANISM: Homo sapiens

<400> SEQUENCE: 4

Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Val Glu
                20                  25                  30

Met Lys Arg Arg Asn Lys Ile Gln Pro Cys Leu Ser Lys Pro Ala Phe
            35                  40                  45

Ala Ser Leu Leu Arg Phe His Gln Phe His Pro Phe Leu Cys Ala Ala
        50                  55                  60

Asp Phe Arg Lys Ile Ala Ser Leu Tyr Gly Ser Asp Lys Phe Asp Leu
65                  70                  75                  80

Pro Tyr Gly Met Arg Thr Ser Ala Glu Tyr Phe Arg Leu Ala Leu Ser
                85                  90                  95

Lys Leu Gln Ser Cys Asp Leu Phe Asp Glu Phe Asp Asn Ile Pro Cys
            100                 105                 110

Lys Lys Cys Val Val Val Gly Asn Gly Gly Val Leu Lys Asn Lys Thr
        115                 120                 125

Leu Gly Glu Lys Ile Asp Ser Tyr Asp Val Ile Ile Arg Met Asn Asn
130                 135                 140

Gly Pro Val Leu Gly His Glu Glu Val Gly Arg Arg Thr Thr Phe
145                 150                 155                 160

Arg Leu Phe Tyr Pro Glu Ser Val Phe Ser Asp Pro Ile His Asn Asp
                165                 170                 175

Pro Asn Thr Thr Val Ile Leu Thr Ala Phe Lys Pro His Asp Leu Arg
            180                 185                 190

Trp Leu Leu Glu Leu Leu Met Gly Asp Lys Ile Asn Thr Asn Gly Phe
        195                 200                 205

Trp Lys Lys Pro Ala Leu Asn Leu Ile Tyr Lys Pro Tyr Gln Ile Arg
210                 215                 220

Ile Leu Asp Pro Phe Ile Ile Arg Thr Ala Ala Tyr Glu Leu Leu His
225                 230                 235                 240

Phe Pro Lys Val Phe Pro Lys Asn Gln Lys Pro Lys His Pro Thr Thr
                245                 250                 255

Gly Ile Ile Ala Ile Thr Leu Ala Phe Tyr Ile Cys His Glu Val His
```

```
            260                 265                 270
Leu Ala Gly Phe Lys Tyr Asn Phe Ser Asp Leu Lys Ser Pro Leu His
            275                 280                 285

Tyr Tyr Gly Asn Ala Thr Met Ser Leu Met Asn Lys Asn Ala Tyr His
            290                 295                 300

Asn Val Thr Ala Glu Gln Leu Phe Leu Lys Asp Ile Ile Glu Lys Asn
305                 310                 315                 320

Leu Val Ile Asn Leu Thr Gln Asp
            325

<210> SEQ ID NO 5
<211> LENGTH: 346
<212> TYPE: PRT
<213> ORGANISM: Homo sapiens

<400> SEQUENCE: 5

Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Glu Ala Ser
                20                  25                  30

Phe Gln Val Trp Asn Lys Asp Ser Ser Lys Asn Leu Ile Pro Arg
            35                  40                  45

Leu Gln Lys Ile Trp Lys Asn Tyr Leu Ser Met Asn Lys Tyr Lys Val
50                  55                  60

Ser Tyr Lys Gly Pro Gly Pro Gly Ile Lys Phe Ser Ala Glu Ala Leu
65                  70                  75                  80

Arg Cys His Leu Arg Asp His Val Asn Val Ser Met Val Glu Val Thr
                85                  90                  95

Asp Phe Pro Phe Asn Thr Ser Glu Trp Glu Gly Tyr Leu Pro Lys Glu
            100                 105                 110

Ser Ile Arg Thr Lys Ala Gly Pro Trp Gly Arg Cys Ala Val Val Ser
            115                 120                 125

Ser Ala Gly Ser Leu Lys Ser Ser Gln Leu Gly Arg Glu Ile Asp Asp
            130                 135                 140

His Asp Ala Val Leu Arg Phe Asn Gly Ala Pro Thr Ala Asn Phe Gln
145                 150                 155                 160

Gln Asp Val Gly Thr Lys Thr Thr Ile Arg Leu Met Asn Ser Gln Leu
                165                 170                 175

Val Thr Thr Glu Lys Arg Phe Leu Lys Asp Ser Leu Tyr Asn Glu Gly
            180                 185                 190

Ile Leu Ile Val Trp Asp Pro Ser Val Tyr His Ser Asp Ile Pro Lys
            195                 200                 205

Trp Tyr Gln Asn Pro Asp Tyr Asn Phe Phe Asn Asn Tyr Lys Thr Tyr
210                 215                 220

Arg Lys Leu His Pro Asn Gln Pro Phe Tyr Ile Leu Lys Pro Gln Met
225                 230                 235                 240

Pro Trp Glu Leu Trp Asp Ile Leu Gln Glu Ile Ser Pro Glu Glu Ile
                245                 250                 255

Gln Pro Asn Pro Pro Ser Ser Gly Met Leu Gly Ile Ile Ile Met Met
            260                 265                 270

Thr Leu Cys Asp Gln Val Asp Ile Tyr Glu Phe Leu Pro Ser Lys Arg
            275                 280                 285

Lys Thr Asp Val Cys Tyr Tyr Tyr Gln Lys Phe Phe Asp Ser Ala Cys
            290                 295                 300
```

```
Thr Met Gly Ala Tyr His Pro Leu Leu Tyr Glu Lys Asn Leu Val Lys
305                 310                 315                 320

His Leu Asn Gln Gly Thr Asp Glu Asp Ile Tyr Leu Leu Gly Lys Ala
            325                 330                 335

Thr Leu Pro Gly Phe Arg Thr Ile His Cys
            340                 345

<210> SEQ ID NO 6
<211> LENGTH: 382
<212> TYPE: PRT
<213> ORGANISM: Clostridium perfringens

<400> SEQUENCE: 6

Met Cys Asn Lys Asn Asn Thr Phe Glu Lys Asn Leu Asp Ile Ser His
1               5                   10                  15

Lys Pro Glu Pro Leu Ile Leu Phe Asn Lys Asp Asn Asn Ile Trp Asn
            20                  25                  30

Ser Lys Tyr Phe Arg Ile Pro Asn Ile Gln Leu Leu Asn Asp Gly Thr
        35                  40                  45

Ile Leu Thr Phe Ser Asp Ile Arg Tyr Asn Gly Pro Asp Asp His Ala
    50                  55                  60

Tyr Ile Asp Ile Ala Ser Ala Arg Ser Thr Asp Phe Gly Lys Thr Trp
65                  70                  75                  80

Ser Tyr Asn Ile Ala Met Lys Asn Asn Arg Ile Asp Ser Thr Tyr Ser
                85                  90                  95

Arg Val Met Asp Ser Thr Thr Val Ile Thr Asn Thr Gly Arg Ile Ile
            100                 105                 110

Leu Ile Ala Gly Ser Trp Asn Thr Asn Gly Asn Trp Ala Met Thr Thr
        115                 120                 125

Ser Thr Arg Arg Ser Asp Trp Ser Val Gln Met Ile Tyr Ser Asp Asp
    130                 135                 140

Asn Gly Leu Thr Trp Ser Asn Lys Ile Asp Leu Thr Lys Asp Ser Ser
145                 150                 155                 160

Lys Val Lys Asn Gln Pro Ser Asn Thr Ile Gly Trp Leu Gly Gly Val
                165                 170                 175

Gly Ser Gly Ile Val Met Asp Asp Gly Thr Ile Val Met Pro Ala Gln
            180                 185                 190

Ile Ser Leu Arg Glu Asn Asn Glu Asn Tyr Tyr Ser Leu Ile Ile
        195                 200                 205

Tyr Ser Lys Asp Asn Gly Glu Thr Trp Thr Met Gly Asn Lys Val Pro
    210                 215                 220

Asn Ser Asn Thr Ser Glu Asn Met Val Ile Glu Leu Asp Gly Ala Leu
225                 230                 235                 240

Ile Met Ser Thr Arg Tyr Asp Tyr Ser Gly Tyr Arg Ala Ala Tyr Ile
                245                 250                 255

Ser His Asp Leu Gly Thr Thr Trp Glu Ile Tyr Glu Pro Leu Asn Gly
            260                 265                 270

Lys Ile Leu Thr Gly Lys Gly Ser Gly Cys Gln Gly Ser Phe Ile Lys
        275                 280                 285

Ala Thr Thr Ser Asn Gly His Arg Ile Gly Leu Ile Ser Ala Pro Lys
    290                 295                 300

Asn Thr Lys Gly Glu Tyr Ile Arg Asp Asn Ile Ala Val Tyr Met Ile
305                 310                 315                 320

Asp Phe Asp Asp Leu Ser Lys Gly Val Gln Glu Ile Cys Ile Pro Tyr
                325                 330                 335
```

```
Pro Glu Asp Gly Asn Lys Leu Gly Gly Gly Tyr Ser Cys Leu Ser Phe
            340                 345                 350

Lys Asn Asn His Leu Gly Ile Val Tyr Glu Ala Asn Gly Asn Ile Glu
            355                 360                 365

Tyr Gln Asp Leu Thr Pro Tyr Tyr Ser Leu Ile Asn Lys Gln
            370                 375             380
```